US00PP17719P3

(12) United States Plant Patent
Layt

(10) Patent No.: US PP17,719 P3
(45) Date of Patent: May 15, 2007

(54) ***DIANELLA REVOLUTA* PLANT NAMED 'DR5000'**

(50) Latin Name: *Dianella revoluta*
Varietal Denomination: DR5000

(75) Inventor: Todd Anthony Layt, New South Wales (AU)

(73) Assignee: Versascapes, LLC, Mt. Pleasant, SC (US)

( * ) Notice: Subject to any disclaimer, the term of this patent is extended or adjusted under 35 U.S.C. 154(b) by 239 days.

(21) Appl. No.: 10/883,942

(22) Filed: Jul. 2, 2004

(65) Prior Publication Data

US 2005/0010986 P1 Jan. 13, 2005

Related U.S. Application Data

(60) Provisional application No. 60/485,661, filed on Jul. 9, 2003.

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

UPOV CDROM 2005/03 Database. Search for cultivar DR5000.* http://www.outdoordesign.com.au/category.act?categoryid=00380#017046 p. 1–3.*

Layt; "*Dianella revoluta* spreading flax lily," *Plant Varieties Journal* 16:2 p. 41 (2003).

Australian Government Department of Agriculture, Fisheries and Forestry, Database entry for Australian Plant Breeders Right Application No. 2002/132; Variety 'DR5000' http://www.affa.gov.au/content/pbr_database/plant_detail.cfm?AID=441396.

* cited by examiner

*Primary Examiner*—Kent Bell
*Assistant Examiner*—Annette H Para
(74) *Attorney, Agent, or Firm*—Myers Bigel Sibley & Sajovec

(57) ABSTRACT

'DR5000' is a distinctive variety of *Dianella revoluta,* which is characterized by its combination of bluish leaf color, short height, upright growth habit, very dense shoots, and narrow-to-medium leaf blade.

1 Drawing Sheet

Latin name of the genus and species: The Latin name of the novel variety disclosed herein is *Dianella revoluta* 'DR5000'.

Variety denomination: The inventive variety of *Dianella revoluta* disclosed herein has been given the variety denomination 'DR5000'.

BACKGROUND OF THE INVENTION

The present invention relates to a new and distinct variety of evergreen perennial *Dianella revoluta,* which has been named 'DR5000'. *Dianella* are a genus of ornamental grass-like plants. In general, *Dianella revoluta* has flax-like leaves with curved edges. Deep blue flowers on stems up to one meter high typically develop in spring and early summer and are followed by blue berries.

An application for plant breeders' rights for 'DR5000' has been lodged with the Australian Plant Breeders Rights Office, which was received on May 23, 2002 and accepted on Jul. 12, 2002 (under Application No. 2002/132).

Parentage: The cultivar 'DR5000' was discovered in 1996 in Clarendon, New South Wales, Australia, during a seedling selection of cultivated *Dianella revoluta* 'DR4000' (unpatented). The parent 'DR4000' is characterized by a wide leaf, tall plant height, and medium plant density. Selection criteria for 'DR5000' were bluish leaf color, strong glaucosity and compact habit.

Asexual reproduction. The new variety 'DR5000' was first asexually propagated by vegetative division in the state of New South Wales, Australia in September 1998 and has been asexually propagated since that time by division and micropropagation. The distinctive characteristics of cultivar 'DR5000' have remained stable and true to type through successive cycles of asexual propagation.

SUMMARY OF THE INVENTION

'DR5000' is a distinctive variety of *Dianella revoluta,* which is characterized by its combination of bluish leaf color, short height, upright growth habit, very dense shoots, and narrow-to-medium leaf blade. Thus far, 'DR5000' has only very rarely been observed to flower.

BRIEF DESCRIPTION OF THE DRAWINGS

FIG. 1 shows an exemplary mature *Dianella revoluta* 'DR5000' plant at approximately 18 to 24-months of age. The plant was propagated in a greenhouse and was transferred to the field at six months and grown out in full sun.

DETAILED BOTANICAL DESCRIPTION OF THE VARIETY

The following is a detailed botanical description of a new and distinct variety of *Dianella revoluta* known as 'DR5000' based upon observations of 15-month old plants grown in nursery pots in full sun in open beds in Clarendon, New South Wales, Australia during summer 2002–autumn 2003

(as described below in connection with Table 1). Plant observations and descriptions were taken in autumn 2003.

Those skilled in the art will appreciate that certain characteristics will vary with older or, conversely, with younger plants. 'DR5000' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on The Royal Horticultural Society Colour Chart, The Royal Horticultural Society, London, 1995 edition.

'DR5000' is an evergreen perennial *Dianella revoluta.* 'DR5000' is a narrow-to-medium bladed, compact plant, with a bluish leaf color. These characteristics are unusual for *Dianella revoluta,* as these plants are usually not very compact and not as blue in color as 'DR5000'. A botanical description of 'DR5000' and comparisons with other varieties of *Dianella revoluta* are provided below.

Technical Description of the Variety

Plant characteristics: Growth habit upright, height short, very dense shoots.

Leaves: Attitude upright, width medium (mean 7.5 mm), average length 25–26 cm, upper side color yellow green (RHS 147A), lower side color greyed green (RHS 189A), glaucosity strong, shape ligulate, apex acute, cross section concave, margin flat-to-weakly revolute.

Basal sheath: Anthocyanin coloration red-purple.

Basal shoots: Attitude upright, arrangement cluster.

Flowers and berries: 'DR5000' has only very rarely been observed to produce flowers or berries and only in Queensland, Australia. This characteristic is unusual for *Dianella revoluta,* which generally bloom regularly beginning in the second or third year. When present, the flowers and berries of 'DR5000' are similar to those produced by the species but are generally less abundant.

Cold and heat tolerance: 'DR5000' has been observed to be cold tolerant to −12° C. in Clarendon, New South Wales, Australia. Foliage color did not change under these conditions, except for a slight burning at the very tips of the leaves. The plant has also been grown for two years in Charleston, S.C., USA and has remained evergreen down to −6° C. Further testing for cold tolerance at high altitude (over 3000 feet) is ongoing.

'DR5000' is also very heat tolerant. It adapted well to the high heat conditions during summer in Clarendon, New South Wales, Australia and high heat and humidity conditions during summer in Charleston, S.C., USA without any noticeable disease or insect damage.

Drought tolerance: Very good drought tolerance; 'DR5000' survived three months without rainfall under hot conditions in non-irrigated garden beds in Clarendon, Australia in Summer, 2002. 'DR5000' has also been grown in non-irrigated beds in Charleston, S.C., USA for two years, and has been observed to go as long as 45 days without rainfall.

Pest resistance: No known pests.

Cultural conditions: 'DR5000' can tolerate low nutrient conditions; it does not like continually wet soil conditions, but can tolerate well-draining sandy soils to very heavy clay soils. pH characteristics of the variety are fairly adaptable.

These and other features and characteristics of 'DR5000' are apparent from FIG. 1.

Comparisons with other *Dianella*

'DR5000' is a more attractive ornamental grass-like plant as compared with the parent 'DR4000'. 'DR5000' is characterized by a bluish leaf color, narrower leaf blade, and more compact plant habit with denser shoots and a shorter plant height as compared with 'DR4000'. The appearance of 'DR5000' is bluish, whereas 'DR4000' is more yellow-green in color (see Table 1).

*Dianella* 'DR2000' (unpatented) is the most similar comparator variety to 'DR5000'. In comparison with 'DR2000', cultivar 'DR5000' has a bluish leaf color whereas 'DR2000' is more yellow-green, has a slightly wider leaf, and has a more compact habit with a shorter plant height and denser shoots than 'DR5000' (see Table 1).

A comparative trial of *Dianella* cultivar 'DR5000' with 'DR4000' and 'DR2000' was carried out in Summer 2002 to Autumn 2003 in Clarendon, New South Wales, Australia. The data are presented in Table 1 below. The plants for this trial were propagated from divisions, planted in to 130-mm pots filled with soilless potting mix, and moved into 140 mm pots in full sun for nine months before the trial started. Nutrition was maintained with slow release fertilizers; pest and disease treatments were applied as needed. The trial was designed such that twenty plants of each variety were arranged in a completely randomized manner. Measurements were taken from ten plants at random with one sample per plant.

TABLE 1

| | *Dianella* Variety | | |
|---|---|---|---|
| Characteristic | 'DR5000' | 'DR2000' | 'DR4000' |
| Plant Height (cm) | | | |
| Mean | 29.8 cm | 36.9 | 54.0 |
| Std Deviation | 2.6 | 4.0 | 6.2 |
| LSD/Sig. | 5.14 | P ≦ 0.01 | P ≦ 0.01 |
| Density of Shoots | Very Dense | Medium Density | Very Dense |
| Leaf Width (mm) | | | |
| Mean | 7.5 | 5.8 | 10.3 |
| Std Deviation | 0.5 | 1.1 | 1.1 |
| LSD/Sig. | 1.10 | P ≦ 0.01 | P ≦ 0.01 |
| Leaf Glaucosity | Strong | Weak | Weak |
| Leaf Color | | | |
| Upper Side | 147A | 147A | 147A |
| Lower Side | 189A | 147B | 147A–B |
| Basal Sheath Color | Red Purple | Reddish Brown | Red Purple |

That which is claimed is:

1. A new and distinct variety of *Dianella revoluta* plant named 'DR5000', substantially as described and illustrated herein.

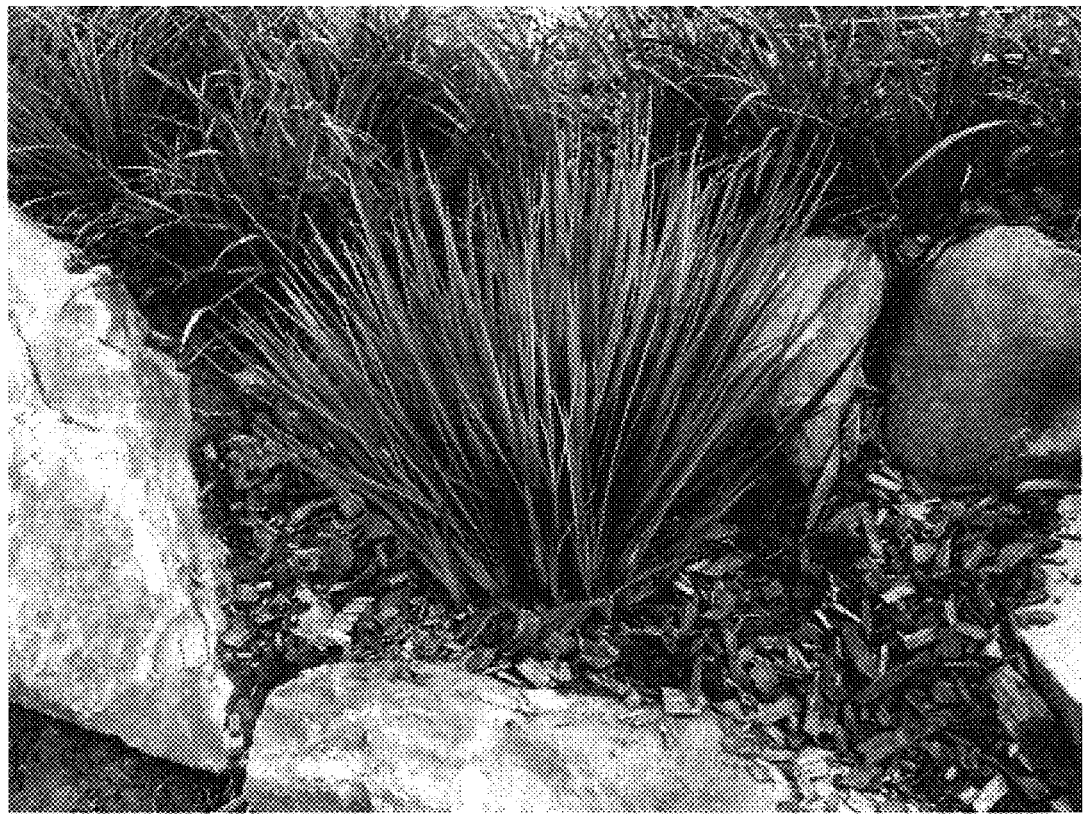

* * * * *